United States Patent [19]

Modrovich

[11] 4,409,326
[45] Oct. 11, 1983

[54] STABILIZED ENZYMATIC SOLUTIONS AND METHOD FOR DETERMINING TOTAL CHOLESTEROL IN HUMAN SERUM

[76] Inventor: Ivan E. Modrovich, 1043 Mesa Dr., Camarillo, Calif. 93010

[21] Appl. No.: 308,162

[22] Filed: Oct. 2, 1981

Related U.S. Application Data

[63] Continuation of Ser. No. 168,204, Jul. 10, 1980, abandoned, which is a continuation-in-part of Ser. No. 68,911, Aug. 23, 1979, abandoned.

[51] Int. Cl.$^3$ .......................... C12Q 1/60; C12Q 1/26; C12Q 1/28; C12N 9/96
[52] U.S. Cl. .......................... 435/11; 435/19; 435/25; 435/28; 435/188; 435/810; 436/71
[58] Field of Search .............. 435/11, 19, 188, 25, 435/28, 810; 23/230 B; 252/408 R; 436/13, 71, 150

[56] References Cited

U.S. PATENT DOCUMENTS

| | | | |
|---|---|---|---|
| 3,876,375 | 4/1975 | Maurukas | 252/408 |
| 4,045,296 | 8/1977 | Sternberg | 435/11 |
| 4,143,080 | 3/1979 | Harders et al. | 435/11 |
| 4,161,425 | 7/1979 | Perry | 435/11 |
| 4,186,251 | 1/1980 | Tarbutton | 435/11 |
| 4,212,938 | 7/1980 | Gruber et al. | 435/11 |
| 4,226,713 | 10/1980 | Goldberg | 435/11 |

FOREIGN PATENT DOCUMENTS

1435400  5/1976  United Kingdom .................. 435/11

OTHER PUBLICATIONS

Allain, C. C. et al., "Enzymatic Determination of Total Serum Cholesterol"; Clinical Chem., vol. 20, No. 4, pp. 470–475 (1974).

Primary Examiner—Benoit Castel
Attorney, Agent, or Firm—Christie, Parker & Hale

[57] ABSTRACT

Stabilized enzymes useful in the diagnostic assay of total cholesterol are prepared by combining three separately prepared reagents: (1) a cholesterol esterase reagent; (2) cholesterol oxidase reagent; and (3) a saline diluent reagent. The cholesterol esterase reagent is prepared by dissolving a salt of cholic acid in a buffer solution providing a pH within the range of about 4 to about 9. To this solution is added a cholesterol esterase. The solution is then mixed with a polyhydroxy organic compound and TRITON-X-100. A cholesterol oxidase and a polyhydroxy organic compound are each dissolved in separate portions of buffer solution to make the cholesterol esterase reagent. The saline diluent solution is prepared by dissolving potassium iodide in water and adding a polyhydroxy organic compound. The resultant three reagents, when combined, provide a stabilized enzyme solution having utility in the total cholesterol assay of a serum sample. The combined reagents have utility in a total oxygen consumption method of analysis of total cholesterol, which analysis method is also disclosed.

27 Claims, 1 Drawing Figure

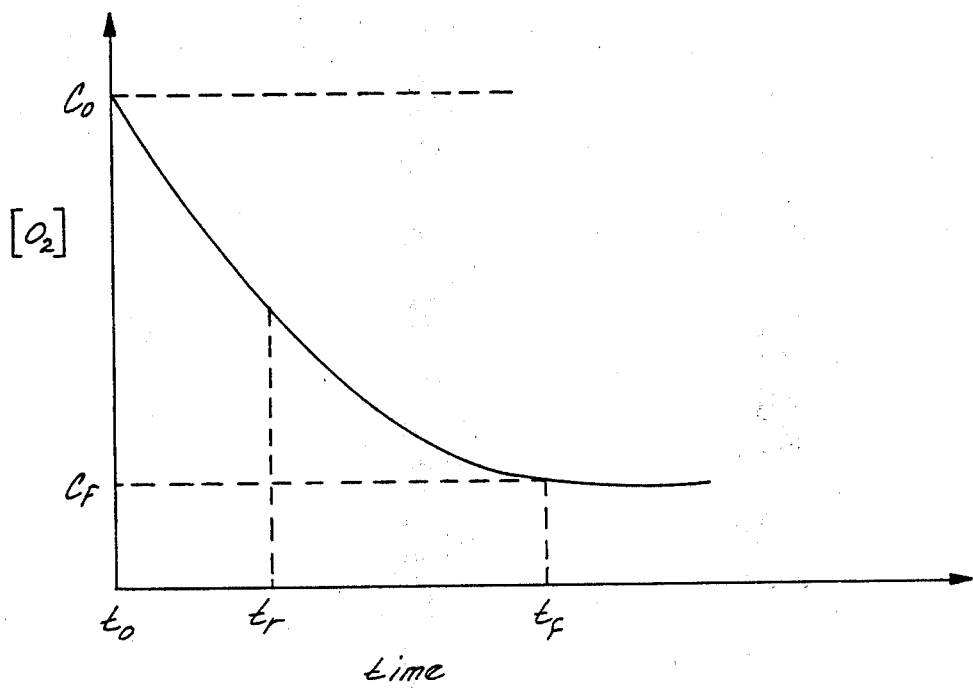

STABILIZED ENZYMATIC SOLUTIONS AND METHOD FOR DETERMINING TOTAL CHOLESTEROL IN HUMAN SERUM

CROSS-REFERENCE TO RELATED APPLICATIONS

This application is a continuation of U.S. application Ser. No. 168,204, filed July 10, 1980 now abandoned, which is a continuation-in-part of U.S. Ser. No. 68,911, filed on Aug. 23, 1979, and titled ENZYMATIC METHOD AND STABILIZED SOLUTIONS FOR DETERMINING TOTAL CHOLESTEROL IN HUMAN SERUM, now abandoned.

BACKGROUND OF THE INVENTION

The present invention relates to a method for determining cholesterol, either total cholesterol or bound cholesterol, in human serum. More particularly, the invention relates to a method and stabilized enzymatic solutions for use in the method in determining the total cholesterol in serum.

Cholesterol is present in biological matter, such as serum and the like, partially in free form and partially in bound form as a cholesterol ester. For the determination of total cholesterol, it is necessary to release the cholesterol that is bound in cholesterol ester form. The releasing of the bound cholesterol has been conducted through saponification of the cholesterol ester under alkaline conditions using alcoholic potash lye, for example. Following the saponification, the released cholesterol can then be determined either chemically or enzymatically by one of the known methods. A chemical determination may be performed with or without saponification, for example, by the Liebermann-Burchard method. An enzymatic determination may be performed by means using cholesterol oxidase, cholesterol esterase, or cholesterol dehydrase.

The alkaline saponification of bound cholesterol is a troublesome and time consuming step in the overall assay of total cholesterol. Furthermore, the relatively aggressive reagents used may lead to a decomposition of the cholesterol. In order to prevent such decomposition and inhibit the determining of false and/or imprecise results of the analysis, a hydrolysis must generally be performed under relatively mild conditions. This, in turn, undesirably increases the length of time required for the cholesterol determination. The alkaline liberation of the bound cholesterol is especially disadvantageous when the determination of cholesterol is to be performed by the preferred enzymatic methods. Since the enzymes are inactivated in the strongly alkaline medium, the hydrolyzate must be neutralized by the addition of acid to a pH of about 5 to 8 before the enzymatic determination can be initiated. This extra step results in the addition of more time in the overall determination of the total cholesterol.

It is also known that bound cholesterol can be freed by the action of enzymes, cholesterol esterase, which break the ester bond in cholesterol esters. Such cholesterol esterases were isolated initially from animal sources, such as from pork pancreas and rat pancreatic juice. It is also known that in addition to cholesterol esterases being found in the pancreas, that cholesterol esterases can be found in the liver.

Allain, et al describe an enzymatic method for the determination of total serum cholesterol using a cholesterol esterase isolated from pork pancreas and rat pancreatic juice, "Clinical Chemistry," 20 (1974), 470–475. In the method of Allain, et al the cholesterol esterase (cholesterol ester hydrolyase), freed the esterified cholesterol. The resulting freed cholesterol was treated with cholesterol oxidase to form cholestenone and hydrogen peroxide. The resulting hydrogen peroxide was measured quantitatively using spectrophotometric methods. The hydrogen peroxide reacted with 4-aminoantipyrine and phenol in the presence of a peroxidase to form a quinoneimine dye. Allain, et al utilized one aqueous buffered solution to conduct the cholesterol determinations. Cholesterol esterases are known labile compounds that are generally unstable in aqueous solutions. Allain, et al state that the enzyme solution used in their method is unstable having a stability of eight hours at room temperature (25° C.) and 24 hours at refrigerated temperatures of 4° C.

U.S. Pat. No. 3,925,164 to Beauchamp, et al also describes a method for the enzymatic determination of total cholesterol in serum. The method therein treats the serum sample with a cholesterol esterase to release the bound cholesterol. The total cholesterol is then determined by known techniques. The method utilizes a cholesterol esterase produced from a microorganism rather than using a cholesterol esterase produced from an animal source. The patent states that the microorganism produced cholesterol esterase is preferred over cholesterol esterase produced from animal sources in the complete saponification of cholesterol esters in the framework of a quantitative analysis process because the cleavage rates for animal source cholesterol esterases were not quantitative. Furthermore, bound cholesterol is present in biological matter in the form of widely different acids. For an enzymatic process to be useful in the framework of a process of quantitative analysis, it is required that all of the esters that may occur be cleaved quantitatively with approximately the same speed and with the same reliability. Many of the known animal-source cholesterol esterases are somewhat specific toward specific cholesterol esters. The activity of such cholesterol esterases is known to vary with regard to various cholesterol esters.

Although the cholesterol esterases produced from microorganisms offer advantages over those produced from animal sources, the microorganism-produced cholesterol esterases also are labile compounds that tend to undergo chemical change in solution and especially in aqueous solutions, which decreases their enzymatic activity. Stability of enzymatic solutions used in diagnostic assays is important in providing methods of analysis which exhibit precision and uniformity among separate determinations when conducted over a period of elapsed time. Instability of enzymatic solutions, in addition to not providing reproducibility of assays, can also add to the ever increasing cost of medical services because the unstable enzymatic solutions need to be discarded and fresh solutions formulated.

It has recently been estimated that about 25 percent of all in vitro diagnostic tests conducted annually in the United States are unreliable. Unreliable tests can result in unnecessary medical treatment, the withholding of necessary treatment and lost income. Because of their high specificity, the use of enzyme determinations has significantly increased during the last few years and indications are that this trend will continue. However, rigorous quality control measures are required to assure the accuracy and consistency of results. This requirement derives from the fact that the exact nature of enzymes, as well as mechanisms of their reactions, remains unknown for the most part.

At present, the greatest limitation in the diagnostic reagent manufacture, by far, lies in the unstable characteristics of the enzymatic solutions. Current cholesterol diagnostic methodologies require the use of labile ingredients whether utilizing enzymes from microorganisms or animal source. Due to the labile nature of the enzymes, rigorous quality control is required over the production of such enzymatic solutions and in reconstituting dry media preparations and formulation of such enzymatic solutions. Such quality control is costly. Moreover, if such control in any step in the process is not maintained within a high degree of control standards, the quality of the final product can be reduced materially leading to decreased precision in assay results.

The present commercial state-of-the-art used for stabilizing the reactive ability of enzymes or coenzymes is by locking them into a solid matrix, either by freeze drying, dry blending such as used for tableting dry powders primarily in the pharmaceutical diagnostic and related industries, and immobilization by locking the chemical structure of the enzyme into a solid matrix. Contrary to the sophistication these terms imply, these approaches are neither practical nor desirable and are also expensive. The manufacturer is forced to remove the water and supply a partial product, thus relinquishing part of the quality control cycle in the dilution and use of the final product. Laboratories are forced to pay the high cost of packaging, reagent waste, freeze drying and dry blending. Usefulness of the product is further limited by packaging modes and sizes.

Furthermore, good product uniformity is difficult to achieve, especially in the laboratories where the products are to be utilized in diagnostic assay. This condition is exemplified by the fact that most commercial freeze-dried controlled sera (reference serum) lists the acceptable bottle-to-bottle variation of enzyme constituents at $\pm 10$ percent of the mean.

The present invention is uniquely designed so that the enzyme solution, although containing labile ingredients in a liquid reagent, are effectively "stabilized" thereby controlling the activity of the labile ingredients in the liquid solution. The means of stability insures long-term stability in a liquid media. Moreover, close tolerance control can be achieved in the manufacturing of a high quality product which eliminates the inconvenience of the rigid package size, the high cost of packaging and freeze drying, and reagent waste.

SUMMARY OF THE INVENTION

Labile enzymes, useful in the diagnostic assay of total cholesterol in serum, are treated according to the invention resulting in long-term stability without deleteriously affecting enzyme activity or photometric absorptivity. The invention provides reagents wherein quality control is assured throughout manufacturing, packaging, storage, and the use. The inconvenience of rigid package size is eliminated as is the high cost of packaging, freeze drying, and reagent waste. The liquid enzyme system for total cholesterol assay, as described herein, provides desired flexibility to total cholesterol assay determination. The stabilized enzymes of the invention have been assessed in studies which compared the liquid stabilized enzyme solutions with fresh reagents. The studies show a one-to-one correlation between aged liquid and fresh reagents with compatible sensitivity and precision. Providing reagents of this type in a stable liquid form enhances the color of spectrophotometric capability of present-day methodologies, as well as other non-color methodologies. The stable liquid enzymes for total cholesterol determination are especially advantageous in an oxygen consumption method of analysis more fully set forth herein. The liquid system of the present invention also offers better reagent homogeneity and packaging, as well as flexibility and usage, in contrast to the freeze dried or dry media preparations.

In diagnostic cholesterol assay, the stabilization of the labile components and particularly the labile cholesterol esterases and oxidases in a ready-to-use liquid media, is a new and exciting approach to satisfy the needs of the clinical laboratory and the reliability demands of the regulatory authorities. The flexibility of these liquid systems insures their applicability to automated instrumentation, as well as their convenience in manual testings.

Stabilization of the enzymes useful in the determination of total cholesterol in serum is accomplished, in accordance with the invention, by preparing three separate solutions which upon combining provide a stabilized enzyme solution for determining total cholesterol by the UV absorption method herein. The first solution, hereinafter referred to as the CHEST reagent, is prepared by dissolving the sodium salt of cholic acid in a buffer solution capable of maintaining the pH within the range of about 6 to about 8. The cholesterol esterase is added to the cholic acid dissolved in the buffer solution. The resultant mixture is thoroughly intermixed. TRITON-X-100 and glycerol are added. The second solution, hereinafter referred to as the CHOX reagent, is prepared by dissolving cholesterol oxidase in a separate portion of the buffer solution and adding glycerol to complete dissolution. The third solution, hereinafter referred to as the DILUENT reagent, is prepared by dissolving potassium iodide (KI) in water then adding glycerol to the solution. The resulting three solutions can then be dispensed into appropriate bottles for storage and subsequent use. Projected shelf-life of the solutions in this form is from about two years to about three years.

The three reagents are combined to form one stabilized combined reagent which has utility in the method herein of total oxygen consumption analysis or in an oxygen rate consumption analytical method as known in the art, such as by using a Beckman Instruments, Inc. Cholesterol Analyzer 2, which is described in co-pending U.S. patent application Ser. No. 68,911, the entire disclosure of which is incorporated herein by this reference.

The method herein for analysis of total cholesterol by measurement of total oxygen consumption is performed by combining the CHEST reagent, CHOX reagent and DILUENT reagent to form a combined reagent. The combined reagent is stable for about 18 months under refrigerated conditions. A portion of the combined reagent is introduced to a cell having an oxygen electrode immersed therein. The concentration of oxygen in the portion of combined reagent is measured. A sample for which the total cholesterol is to be determined is then introduced to the combined reagent in the cell. When the sample is introduced to the combined reagent the following reaction sequences occur:

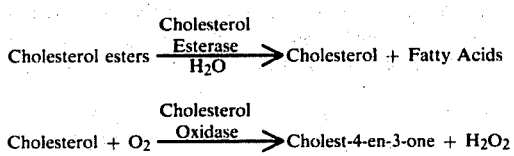

The cholesterol esters present in the sample are broken down by the activity of the cholesterol esterase forming cholesterol and fatty acids. The cholesterol formed and any free cholesterol initially within the sample reacts with dissolved oxygen in the liquid in the cell to form cholestenone and hydrogen peroxide. The amount of oxygen consumed is then measured and correlated to the amount of cholesterol present in the sample.

These and many other features and attendant advantages of the invention will become apparent as the invention becomes better understood by reference to the following detailed description.

BRIEF DESCRIPTION OF THE DRAWING

The stabilized enzyme solutions and method of analysis of total cholesterol using oxygen consumption will be better understood with regard to the following detailed description and accompanying drawing which represents a curve showing the relationship of oxygen consumed in time for the reaction of enzyme de-esterification of cholesterol esters and subsequent enzymic oxidation of cholesterol to cholestenone.

DETAILED DESCRIPTION OF THE INVENTION

The method and stabilized solutions described herein can be used in the clinical diagnostic field for the determination of total cholesterol in serum. The following chemical reaction sequence illustrates the methodology of total cholesterol determination using the stabilized solutions herein:

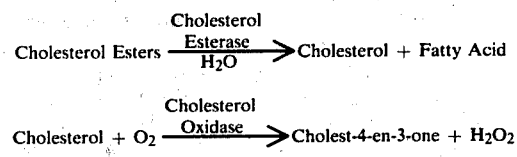

In the cholesterol assay method illustrated by the above reaction sequence, cholesterol ester bonds are split by the cholesterol esterase to form free cholesterol and the appropriate fatty acid. The cholesterol then reacts with oxygen in the presence of cholesterol oxidase to form the ketone, cholest-4-en-3-one, and hydrogen peroxide. It is the reaction sequence (II) above that has been developed for quantitative measurements for determining the amount of cholesterol present in a serum sample. Generally, heretobefore, the quantitative determination of cholesterol was made by measuring the production of hydrogen peroxide or the rate of consumption of oxygen.

When the production of hydrogen peroxide is used, generally a color-producing agent is used which reacts with the hydrogen peroxide to produce a chromogen, providing color which is measurable quantitatively by spectrophotometric analysis. Such an analytical method using 4-aminoantipyrine as a color-producing compound is described in U.S. Ser. No. 68,911.

When cholesterol analysis is made by measuring the consumption of oxygen, the rate of oxygen consumption can be measured by an instrument which relates the rate of oxygen consumption to the total cholesterol concentration. The rate of oxygen consumption may be measured using an oxygen electrode. An instrument for measuring the consumption of oxygen utilizing an oxygen electrode is available commercially from Beckman Instruments, Inc., a Cholesterol Analyzer 2. The oxygen electrode responds to oxygen concentration in the sample/reagent solution into which it is immersed. The oxygen electrode is a polarographic electrode in that it measures a current limited by the diffusion of oxygen through a membrane to the cathode. A stable, fixed thickness of an electrolyte gel is maintained between the membrane and cathode. The amount of oxygen which diffuses through the membrane is proportional to the oxygen concentration in the solution. Associated electronic circuitry differentiates the electrode output signal providing a signal which is proportional to the rate of oxygen consumption at an empirically determined time following the addition of the sample being analyzed. The rate of oxygen consumption is calibrated empirically using standard solutions containing known cholesterol concentrations. The rate of oxygen consumed after a given time can then be correlated to the cholesterol concentration. The oxygen consumption rate analysis has a drawback in that the rate is measured at an arbitrarily selected time. Although the time can be determined empirically that will provide the best reproducibility of cholesterol determinations, the possibility exists that not all the cholesterol is being measured. Problems that can lead to poor reproducibility of results include carry-over of cholesterol in the cell between determination and lack of certain cholesterol esters being broken down to cholesterol in the preselected time.

It has been found that the enzyme solutions herein have and retain sufficient activity to provide good precision and assay of cholesterol when formulated by the method described herein.

For ease of description of the stabilized solutions, the solutions will be described herein with regard to the method of total oxygen consumption analysis.

The buffer solutions used in formulating the reagents herein comprise a buffer solution which is capable of maintaining the pH of the reagent within a range from about 4 to about 9. A preferred buffer is prepared by dissolving potassium dihydrogen phosphate in water and adding sodium hydroxide to provide the desired pH within the above range or preferred range of 6 to 8. A particularly preferred pH for such a formulated buffer solution is a pH of about 6.60. The buffer is selected which provides the proper pH ranges and which does not materially interfere with the enzyme activity or the reactions occurring within the cholesterol assay determination. The above-described potassium dihydrogen phosphate buffer solution is particularly preferred because it provides the desired pH range and does not otherwise interfere with any of the enzyme reactions occurring in the cholesterol determination.

The CHEST reagent containing the cholesterol esterase enzymes is prepared by dissolving cholesterol esterase in the buffer solution having a pH within the range of about 4 to about 9. The sodium salt of cholic acid is added to assist in dissolving the cholesterol esterase in the buffer solution, and to assist in breaking up any lipoproteins in the sample to be assayed for cholesterol. The lipoproteins contain esters of cholesterol. Any metal salt such as an alkali metal salt of cholic acid can be used, however, the sodium salt is preferred because it is readily available commercially and the presence of the sodium ion in the solution does not deleteriously affect the solution nor the cholesterol assay. The sodium salt of cholic acid (sodium cholate) is added to the mixture of cholesterol esterase and buffer solution to provide activation of the cholesterol esterase to assist in the stabilization of the resulting enzyme solution, and to break up lipoproteins present in serum samples during assay. Sodium cholate is available commercially and the commercially available sodium cholate is acceptable for use in the solutions described herein. However, the commercial preparations of sodium cholate contain some impurities which can tend to deactivate the enzymes. For this reason, it is desirable to use a small amount of sodium cholate when formulating the enzyme solution. For example, sodium cholate is used in an amount to provide about a 0.01 to 10 mM (millimolar) solution of sodium cholate. When combined with the other two reagents, such an amount of sodium cholate does not inhibit the enzyme activity to any substantial degree.

The cholesterol esterase can be any cholesterol esterase. It is preferred that the cholesterol esterase be produced from a microbial source. Such microbial-produced cholesterol esterase is preferred because it has better stability and activity in the assay media than a cholesterol esterase produced from an animal source. In addition, the cholesterol esterase from a microbial source is preferred because cholesterol esterase from animal source is generally contaminated with proteases which can react with cholesterol oxidase thereby deactivating the cholesterol oxidase and making it unavailable for reacting with cholesterol to produce the cholestenone. A preferred cholesterol esterase is a cholesterol esterase produced from pseudomonas fluorescens. The preferred cholesterol esterase is obtained from pseudomonas fluorescens ATCC 21156 commercially available from Kyowa Hakko Kogyo Company, Ltd.

The cholesterol esterase can be used in any amount to provide the desired activity in the enzyme solution. The activity of the cholesterol esterase desired is that amount which will provide an activity in the final combined reagent solution of greater than about 50 IU/liter. The more cholesterol esterase present, the faster the reaction will go to completion. However, the upper limit is subject to economical limits. An amount of cholesterol esterase in the CHEST reagent can be about 10,000 IU/l. Cholesterol esterases can also be obtained from microorganisms other than pseudomonas fluorescens, for example, cholesterol esterases can be obtained from microorganisms, as described in U.S. Pat. No. 3,925,164 of Beauchamp, et al, the entire disclosure of which is incorporated herein by this reference.

Following the mixing of cholesterol esterase, sodium cholate and buffer solution, the mixture is allowed to stand under refrigeration for about 24 hours. The mixture is thoroughly mixed to obtain a homogeneously opaque solution. To this solution is added a polyhydroxy compound, such as ethylene glycol, propylene glycol and glycerol. Glycerol is particularly preferred as the glycerol does not inhibit the enzyme activity, nor does it deleteriously affect the cholesterol assay. The polyhydroxy compound is used in an amount which provides about one-half the volume of the reagent solution. The amount of polyhydroxy compound can be greater but such higher amounts can reduce the enzyme activity and thereby make the cholesterol assay completion time longer. Greater amounts of the polyhydroxy compound also can increase the viscosity of the enzyme solution thereby making analysis by instrumental means more difficult.

In addition to the polyhydroxy compound, there is added an alkyl aryl polyether alcohol, TRITON-X-100 (a registered trademark product of Rohm & Haas, Co.). TRITON-X-100 is commercially available from Eastman Kodak Co. and J. T. Baker Chemical Co. TRITON-X-100 is a polyethylene glycol, p-isooctylphenyl ether, CAS Registry No. 9002-93-1. TRITON-X-100 is designated in McCutcheon's *Detergent and Emulsifiers* as octylphenoxy polyethoxy ethanol. For the purposes of the stabilized solutions herein, the commercially available TRITON-X-100 is acceptable. Especially acceptable is the scintillation grade TRITON-X-100 commercially available from J. T. Baker Chemical Co. and sold under the commercial name LSC Non-Ionic Surfactant Scintrex. The TRITON-X-100 can be added in an amount which will provide at least 0.01 to about 0.5 percent by volume TRITON-X-100 in the combined reagent solution. An amount of TRITON-X-100 greater than about 0.5 percent by volume can be used. However, as the TRITON-X-100 is a surfactant, an amount greater than 0.5 percent can create excessive foaming and therefore is undesirable. Generally, an amount of TRITON-X-100 greater than 0.3 percent by volume does not significantly increase the activity, the stability of esterase, or increase the completion rate of the cholesterol assay. The TRITON-X-100 used in an amount at least about 0.1 percent by volume does activate, i.e., increase the activity of the cholesterol esterase and it has been found that the activity of cholesterol esterase from pseudomonas fluorescens exhibits a reduced activity when amounts of TRITON-X-100 are less than 0.1 percent by volume. Although not to be held to the theory herein, Applicant theorizes that amounts of TRITON-X-100 greater than 0.1 pecent by volume breaks up the lipid characterization of the crude cholesterol esterase thereupon activating the cholesterol esterase. After the addition of the TRITON-X-100, the enzyme solution can be set aside as the CHEST reagent.

The CHOX reagent or cholesterol oxidase reagent is then prepared. Cholesterol oxidase is first dissolved in a buffer solution, which buffer solution is as described above with regard to the CHEST reagent. The cholesterol oxidase is preferably produced from microorganism sources. Cholesterol oxidases from non-microbial sources, such as animal sources, exhibit a much reduced activity in the assay media described herein for cholesterol. The micro-organisms from which an acceptable cholesterol oxidase can be produced are pseudomonas sp, nocardia erythropolis and brevibacterium sterolicum. Cholesterol oxidases from these microorganisms are commercially available and for the purposes of the solutions herein the commercially available cholesterol oxidases are acceptable. Although acceptable enzymes are obtained from the above micro-organisms, the activity of the cholesterol oxidase in the enzyme solution depends upon the source of the cholesterol oxidase and the pH of the assay media. For the enzyme solution herein, the preferred cholesterol oxidase source is nocardia erythropolis. Such a cholesterol oxidase is commercially available from Whatman Chemical Co. The cholesterol oxidase from nocardia erythropolis is preferred as it exhibits a maximum activity at a pH of about 5 to about 9 and preferably between a pH range from about 6 to about 8. The cholesterol oxidase from nocardia erythropolis is especially stable and retains is activity in the enzyme solution herein. The cholesterol oxidase from pseudomonas sp has its maximum activity at a pH of about 5. The cholesterol oxidase produced by brevibacterium stero licum has its maximum activity of pH of about 6.

The cholesterol oxidase can be used in any amount that provides an activity greater than 100 U/l in the combined reagent. Amounts that provide less than 100 U/l are undesired because the time for the assay is increased. Larger amounts of cholesterol oxidase increase the rate of reaction and, therefore, decrease the time required to perform a total cholesterol assay. Because of the stabilizing effect of the solution herein, it has been found that the cholesterol oxidase can be present in an amount of about 15,000 to about 25,000 IU/l of the CHOX reagent and preferably about 20,000 IU/l. This amount of colesterol oxidase is sufficient to provide an acceptable time for a clinical cholesterol assay.

A polyhydroxy compound, such a glycerol, ethylene glycol, propylene glycol, mannitol and sorbitol is added to the solution in an amount up to about one-half the volume of the final combined reagent solution to be formed. A preferred polyhydroxy compound is glycerol. Propylene glycol is not preferred, especially at high concentrations thereof as it can denature the enzymes. The resultant solution is the CHOX reagent.

The third solution, DILUENT solution, is prepared by dissolving potassium iodide in water. The amount of potassium iodide used is an amount that provides about 1 to about 15 percent by weight potassium iodide in the combined reagent. A polyhydroxy compound as described in regard to the CHEST and CHOX reagent can be added before or after dissolving the KI. Glycerol in an amount of about 20 percent by volume is preferred.

This salt solution is important in the analysis for total cholesterol by total oxygen consumption measurement. In the total oxygen consumption analytical method, it is desirable that either reaction (I) or reaction (II) in the above reaction sequence proceed as quickly as possible to completion to enable the total oxygen consumption. To make the reaction sequence (I) proceed instantaneously, there would be required a large activity of cholesterol esterase which is undesirable for economic reasons. Thus, it is preferable to make the second reaction proceed rapidly. However, again it is undesirable economically to increase the cholesterol oxidase activity to too great an extent. It has been found herein that the potassium iodide solution speeds the completion of the reaction sequence (II). The potassium iodide reacts with the hydrogen peroxide formed and by removing this reaction product ($H_2O_2$) the reaction sequence (II) proceeds to the right (products) faster. The potassium iodide is then preferably present in an amount sufficient to make the reaction between the hydrogen peroxide and potassium iodide instantaneous. The potassium iodide concentration is related to the amount of cholesterol oxidase needed. If the potassium iodide concentration is increased then the amount of cholesterol oxidase needed is reduced.

In addition to reducing the amount of cholesterol oxidase that is needed, the potassium iodide also reduces the solubility of atmospheric oxygen thus providing a greater signal per unit change in oxygen in the solutions containing potassium iodide. Therefore, the presence of potassium iodide has an effect of stabilizing the readings on total oxygen concentration present in the analytical cell prior to, during and upon completion of the analysis. The presence of potassium iodide in the combined reagent containing the cholesterol esterase and cholesterol oxidase enzymes also has some salt stabilizing effect on the enzymes but, as can be seen above, other beneficial properties are also provided by the potassium iodide.

Salts other than potassium iodide can be used for their effect on decreasing the solubility of atmospheric oxygen in the reaction mixture. For example, NaCl, KCl and the like can be used as well as increasing the buffer (salt) concentration. However, for the above reasons potassium iodide is preferred.

The water used in the solutions described herein is preferably deionized or distilled water or both. Using such deionized and/or distilled water is preferred to avoid contaminating the solution with impurities which can be present in tap water, although tap water used by the author also yielded accurate results.

A combined reagent is formed by combining and thoroughly intermixing the CHEST reagent, CHOX reagent and DILUENT reagent. The relative amounts of the three reagents are sufficient to provide a combined reagent having the following concentrations:

| Cholesterol esterase | >50 IU/l |
|---|---|
| Cholesterol oxidase | >100 IU/l |
| Buffer | >25 mM up to 1 M |
| Glycerol | >5%–50% v/v (vol/vol) |
| KI | >1%–15% w/w (weight/weight) |
| TRITON-X-100 | >0.01%–0.5% v/v |
| Sodium Cholate | >0.01 mM–10 mM |

The resulting combined reagent solution provides a stabilized solution which can be used in the oxygen consumption method of assay for total cholesterol in a serum sample. The combined reagent solution has a stability of about 18 months under refrigerated conditions (2° to 8° C.), and a stability of about five days at 41° C.

The solution has special applicability when used in a Beckman Cholesterol Analyzer 2 for oxygen consumption rate analysis. The Beckman Cholesterol Analyzer 2 can conduct assay on up to about 50 samples of serum per hour. The instrument can be calibrated using standard reference serums containing known amounts of cholesterol. The volume of the serum and stabilized solution used is approximately one milliliter of the stabilized solution, plus approximately 5 to 10 microliters of the serum sample. The sample introduced into the instrument is generally about five microliters in volume.

The invention is further illustrated by, but not limited to, the following examples.

EXAMPLE I

The first CHEST reagent and stabilized solution is prepared by forming a buffer solution of sodium hydroxide and potassium dihydrogen phosphate. The buffer solution is prepared by dissolving 136 g of potassium dihydrogen phosphate in 980 ml of distilled water. To the resultant solution is added 30 g of sodium hydroxide which is thoroughly intermixed and dissolved in the solution. The resulting buffer solution has a pH of about 6.60.

To 100 ml of the buffer solution is added 1.5 g of sodium cholate. Added to the buffer solution is 2,000 international units (IU) of cholesterol esterase from pseudomonas fluorescans (ATCC 21156), commercially available from Kyowa Hakko Kogyo Company, Ltd. The cholesterol esterase is thoroughly intermixed with the buffer solution and sodium cholate, and the resultant mixture is allowed to stand under refrigerator conditions (2° to 8° C.) for about 24 hours. The resultant mixture is a homogeneously opaque solution.

To the mixture is added 100 ml of glycerol and 3 ml of TRITON-X-100 (scintillation grade) from J. T. Baker Chemical Co. The glycerol and TRITON-X-100 are added simultaneously with stirring to insure thorough intermixing with the buffered cholesterol esterase mixture. The resultant solution is labeled as CHEST reagent and has the following concentrations as formulated:

| | |
|---|---|
| Cholesterol esterase | 10,000 IU/l |
| Sodium cholate | 17.4 mM |
| Buffer (KH$_2$PO$_4$) | 1 M |
| Glycerol | 50% v/v |
| TRITON-X-100 | 1.5% v/v |

Cholesterol oxidase, commercially available from Whatman Chemical Co. and produced from the microorganism nocardia erythropolis or pseudomonas is dissolved in 100 ml of the buffer solution. 4,000 IU cholesterol oxidase is dissolved in the buffer solution. Finally 100 ml of glycerol is added and thoroughly mixed. The resultant CHOX reagent solution of cholesterol oxidase had the following concentration as formulated:

| | |
|---|---|
| Cholesterol oxidase | 20,000 IU/l |
| Buffer (KH$_2$PO$_4$) | 1 M |
| Glycerol | 50% v/v |

The third reagent, DILUENT reagent, is formulated by dissolving potassium iodide in distilled water and adding glycerol. The resultant DILUENT reagent has the following concentration as formulated:

| | |
|---|---|
| KI | 10% w/v |
| Glycerol | 13% v/v |
| Water | to make above |

Prior to conducting an assay of cholesterol in a serum sample the three reagents are combined in the following amounts:
3 parts CHOX reagent
2 parts CHEST reagent
25 parts DILUENT reagent
The combined reagent is then thoroughly intermixed by inverting at least 30 times and filtered through 0.45 micron filter (Gelman). The formulated combined reagent has the following concentration as formulated:

| | |
|---|---|
| TRITON-X-100 | 0.1% v/v |
| KI | 8.3% w/v |
| Sodium cholate | 1.2 MM |
| Glycerol | 19.2% v/v |
| Buffer | 83 mM |
| Cholesterol oxidase | 2000 IU/l |
| Cholesterol esterase | 667 IU/l |

The combined reagents have an appearance that is clear. The pH, at 25° C. for the combined reagent, is 6.7±0.2. The dynamic range of the combined reagents after 18 months of shelf life at 2° to 8° C. is estimated to be about 600 mg/dl based on accelerated stability studies at elevated temperatures. The recovery of the activity when compared with commercial lipid control serum PRECILIP was 95 to 105 percent of the theoretical value for the combined reagent.

The assay of total cholesterol in a serum sample is conducted using 1.0 ml of the combined reagent with five microliters of a serum sample.

The combined reagent has a stability at 41° C. of about five days and at 2° to 8° C. stability is estimated to be about 18 months. The stability is measured to the time which would allow recovery of 95 to 105 percent of the cholesterol value of the lipid control serum PRECILIP. Five times the sample volume is used (i.e., 25 μl of sample per ml of reagent).

The method herein in which the stabilized enzyme solutions have utility is a total oxygen consumption analysis. This method was made possible by the development of the stabilized enzyme solutions herein.

The method comprises the utilization of the de-esterification reaction sequence (I) above of cholesterol esters and the subsequent oxidation of the cholesterol to the ketone, cholest-4-en-3-one, reaction sequence (II) above. In the second reaction sequence, oxygen present within the system is consumed by the reaction. The amount of oxygen consumed can be correlated to the amount of cholesterol present in the sample being analyzed. Heretofore before, the rate of oxygen consumption was measured at an arbitrarily selected time after combining the sample and cholesterol esterase and cholesterol oxidase enzymes. The time was selected as a result of empirical determinations that were conducted on samples having known cholesterol concentrations. The ability to select a given time at which to measure the oxygen consumption rate is based upon all the cholesterol esters present being de-esterified and the cholesterol formed reacting with the oxygen. However, a drawback to the method is the differing reaction rates of various cholesterol esters with regard to differing cholesterol esterases. Thus, if a sample to be analyzed contains cholesterol esters that have different de-esterification times than the cholesterol esters used to determine the measurement time, inaccurate results regarding the total cholesterol in the sample can result. In addition, if when an analysis is made some sample from a previous determination is left in the sample cell, inaccurate results can also be obtained. For example, the rate may proceed faster because of the presence of cholesterol in the previous sample, thus leading to inaccurate measurements at the arbitrarily selected measurement time.

The total oxygen consumption method herein avoids the drawbacks of an oxygen rate analysis. Oxygen consumption in the second reaction sequence (II) above can be illustrated by the curve shown in the accompanying drawing with oxygen concentration plotted on the Y-coordinate and time plotted on the X-coordinate. As shown in the drawing at $t_o$ there is an oxygen concentration of $C_o$. At $t_o$ the combined reagent (mixture of CHEST reagent, CHOX reagent and DILUENT reagent) and sample containing cholesterol and cholesterol esters are mixed. The oxygen concentration begins to drop in a somewhat linear fashion of generally constant slope eventually tapering to a nonsloping line. As the line has a somewhat constant slope, it is along this portion of the line that enables the oxygen rate analysis, such as at $t_r$. As can be seen from the drawing, a change in the initial oxygen concentration (such as through contaminations with previous sample) or change in rate of de-esterification can affect the curve at time $t_r$. At $t_f$ the reaction is essentially completed and the curve becomes non-sloping and eventually will begin to slope upwardly because of reabsorption of atmospheric oxygen by the liquid within the sample cell. The total oxygen consumed by the reaction is essentially the amount of oxygen prepresented by $C_o-C_f$ in the drawing.

The method herein of total oxygen consumption has been made possible by the reagents and especially stabilized enzyme reagents herein. In order to make the method function in a clinically acceptable manner, the first reaction sequence (I) must proceed rapidly to enable the second reaction sequence (II) to proceed to completion within a clinically acceptable time. Applicant has determined that the method of total oxygen consumption can be performed in a clinically acceptable time using the reagents herein. The concentration of oxygen is determined by immersing an oxygen electrode in an aliquot of the combined reagents, then introducing the sample.

The method is conducted by combining the three reagents; CHEST reagent, CHOX reagent, and DILUENT reagent into a combined reagent and thoroughly intermixing. A portion of this combined reagent is then introduced to sample cell. An oxygen detection electrode is immersed in the combined reagent in the sample cell. The oxygen electrode can be a polarographic electrode which can measure a current limited by the diffusion of oxygen through a membrane to a cathode. The amount of oxygen which diffuses through the membrane is proportional to the oxygen concentration in the solution. The concentration of oxygen can be measured and retained in associated electronic circuitry. A sample to be analyzed is introduced to the cell and mixed with the combined reagent. The decrease in oxygen concentration can be monitored if desired, and a printout of the curve can be made through an appropriate printer connected to the oxygen electrode by appropriate associated electronic circuitry. Rather than monitoring the oxygen consumption, the associated electronic circuitry can monitor the oxygen consumption and, when the oxygen consumption has leveled off (reaction sequence (II) essentially complete) a determination of the oxygen consumed can be made by comparing the initial value for the oxygen concentration with the final value through appropriate associated electronic circuitry. The difference in the oxygen concentration values can then be correlated to the amount of cholesterol in the sample.

What is claimed is:

1. An aqueous stabilized enzymic reagent solution for use in determining total cholesterol, comprising cholesterol esterase in an amount greater than 50 U/liter, cholesterol oxidase in an amount greater than 100 U/l, a buffer solution for maintaining the pH within the range of about 4 to 9, a polyhydroxy organic compound in an amount from about 5 to about 50 percent by volume, potassium iodide in an amount from about 1 to about 15 percent by weight, a nonionic surfactant in an amount from about 0.01 to about 0.5 percent by volume and a salt of cholic acid in an amount from about 0.01 mM to about 10 mM.

2. A kit for use in the enzyme assay of total cholesterol comprising:
    (a) a first reagent solution comprising cholesterol esterase dissolved in an an aqueous buffer solution providing a pH range from about 4 to about 9, a polyhydroxy organic compound, a salt of cholic acid and a nonionic surfactant;
    (b) a second reagent solution comprising cholesterol oxidase dissolved in an aqueous buffer solution providing a pH range from about 4 to about 9 and a polyhydroxy organic compound; and
    (c) a third reagent solution comprising a mixture of a salt dissolved in water and a polyhydroxy organic compound, said first reagent, second reagent and third reagent solutions when combined providing a solution having a polyhydroxy organic compound in an amount of from about 5 to about 50 percent by volume.

3. A kit as recited in claim 2 wherein the third reagent comprises a mixture of potassium iodide dissolved in water and a polyhydroxy organic compound.

4. A kit as recited in claim 2 wherein the first reagent comprises about 10,000 U/l (at 30° C. pH 6.6) cholesterol esterase.

5. A kit as recited in claim 2 wherein the first reagent comprises about 10,000 U/l (at 30° C. pH 6.6) cholesterol esterase, about 17.4 mM sodium cholate, about 1.5 percent by volume octylphenoxy polyethoxy ethanol, a buffer solution of $KH_2PO_4$ and NaOH, and about 50% by volume glycerol as the polyhydroxy organic compound.

6. A kit as recited in claim 2 wherein the second reagent comprises about 20,000 U/l (at 37° C. pH 6.6) cholesterol oxidase.

7. A kit as recited in claim 6 wherein the second reagent comprises about 20,000 U/l (at 37° C. pH 6.6) cholesterol oxidase, a buffer solution of $KH_2PO_4$ and NaOH, and about 50 percent by volume glycerol as the polyhydroxy organic compound.

8. A kit as recited in claim 2 wherein the third reagent comprises an aqueous solution of 10 percent by weight potassium iodide dissolved in water and about 13 percent by volume glycerol as the polyhydroxy organic compound.

9. A reagent solution as recited in claim 1 or 2 wherein the buffer solution provides a pH of about 6 to 8.

10. A reagent solution as recited in claim 1 or 2 wherein the cholesterol esterase is from the microorganism pseudomonas fluorescens ATCC 21156.

11. A reagent solution as recited in claim 1 or 2 wherein the cholesterol oxidase is from a microorganism selected from the group consisting of pseudomonas sp, nocardia erythropolis, and brevibacterium stero licum.

12. A reagent solution as recited in claim 1 or 2 wherein the polyhydroxy organic compound is selected from the group consisting of glycerol, ethylene glycol, mannitol, sorbitol, and propylene glycol.

13. A reagent solution as recited in claim 1 or 2 wherein the nonionic surfactant is octylphenoxy polyethoxy ethanol.

14. A method for the enzymic assay of total cholesterol in a sample, the method comprising the steps of:
    (a) preparing a buffer solution providing a pH range from about 4 to about 9;
    (b) preparing a first aqueous reagent solution by dissolving cholesterol esterase and a salt of cholic acid in a mixture comprising a portion of the buffer solution, a nonionic surfactant and a polyhydroxy organic compound;
    (c) preparing a second aqueous reagent solution by dissolving cholesterol oxidase in a mixture comprising a portion of the buffer solution and a polyhydroxy organic compound;

(d) preparing a third aqueous reagent solution by dissolving a salt in water and adding a polyhydroxy organic compound;

(e) combining the first, second and third reagent solutions forming a combined reagent solution in which the polyhydroxy organic compound is present in an amount of from about 5 to about 50 percent by volume;

(f) introducing a portion of the combined reagent solution to an analytic cell;

(g) immersing an oxygen detection electrode capable of measuring the oxygen concentration in a liquid in the portion of combined reagent solution with the analytic cell;

(h) measuring the oxygen concentration in the portion of combined reagent solution;

(i) introducing to the portion of combined reagent solution in the analytic cell a sample for which the total cholesterol is to be determined;

(j) measuring the oxygen concentration of the liquid in the analytic cell when the oxygen concentration remains substantially constant;

(k) determining the amount of oxygen consumed after the introduction of the sample; and (l) correlating the amount of oxygen consumed to the amount of cholesterol in the sample.

15. A method as recited in claim 14 wherein the buffer solution is prepared by dissolving $KH_2PO_4$ and NaOH in water.

16. A method as recited in claim 14 wherein the polyhydroxy compound is selected from the group consisting of glycerol, ethylene glycol, sorbitol, mannitol, and propylene glycol.

17. A method as recited in claim 14 wherein the polyhydroxy organic compound is glycerol.

18. A method as recited in claim 14 wherein the combined reagent solution comprises greater than 50 U/l cholesterol esterase, greater than 100 U/l cholesterol oxidase, a pH between 6 to 8, from about 5 to about 50 percent by volume polyhydroxy organic compound, from about 1 to about 15 percent by weight potassium iodide, from about 0.01 to about 0.5 percent by volume surfactant, and from about 0.01 mM to about 10 mM sodium cholate.

19. A method as recited in claim 14 or 18 wherein the nonionic surfactant comprises octylphenoxy polyethoxy ethanol.

20. A method as recited in claim 14 wherein the first reagent solution comprises 10,000 U/l (at 30° C. pH 6.6) cholesterol esterase, about 50 percent by volume glycerol, a buffer comprising $KH_2PO_4$, NaOH and water providing a pH of about 6 to about 7, about 17.4 mM sodium cholate and about 1.5 percent by volume octylphenoxy polyethoxy ethanol; the second reagent solution comprises 20,000 U/l (at 37° C. pH 6.6) cholesterol oxidase, about 50 percent by volume glycerol and a buffer comprising $KH_2PO_4$, NaOH and water; and the third reagent solution comprises about 10 percent by weight potassium iodide, water and about 13 percent by volume glycerol.

21. A method as recited in claim 20 wherein the combined reagent solution comprises 2 parts of the first reagent solution, 3 parts of the second reagent solution, and 25 parts of the third reagent solution.

22. A method as claimed in claim 14 in which the salt dissolved in the third reagent solution comprises potassium iodide.

23. A kit for use in the enzymic assay of total cholesterol comprising:

(a) a first reagent solution comprising cholesterol esterase dissolved in a buffer solution providing a pH range from about 4 to about 9, a polyhydroxy organic compound, a salt of cholic acid and a nonionic surfactant;

(b) a second reagent solution comprising cholesterol oxidase dissolved in a buffer solution providing a pH range from about 4 to about 9 and a polyhydroxy organic compound; and (c) a third reagent solution comprising a mixture of a potassium iodide dissolved in water and a polyhydroxy organic compound, said first, second and third reagent solutions when combined providing a reagent solution having a pH of from about 4 to 9 for use in determining total cholesterol and comprising cholesterol esterase in an amount greater than 50 U/liter, cholesterol oxidase in an amount greater than 100 U/l, a polyhydroxy organic compound in an amount from about 5 to about 50 percent by volume, potassium iodide in an amount from about 1 to about 15 percent by weight, a nonionic surfactant in an amount from about 0.01 to about 0.5 percent by volume and a salt of cholic acid in an amount from about 0.01 mM to about 10 mM.

24. A kit as claimed in claim 23 in which the salt of cholic acid is sodium cholate.

25. A kit as claimed in claim 24 in which the nonionic surfactant is octylphenoxy polyethoxy ethanol.

26. A kit as claimed in claim 23 in which the polyhydroxy organic compound is selected from the group consisting of glycerol, ethylene glycol, sorbitol, mannitol, and propylene glycol.

27. A kit as claimed in claim 25 in which the polyhydroxy organic compound is selected from the group consisting of glycerol, ethylene glycol, sorbitol, mannitol, and propylene glycol.

* * * * *